United States Patent [19]
Hayashi et al.

[11] 3,985,875
[45] Oct. 12, 1976

[54] ω-(N-ACYLAMINO)ALKYLPHOSPHORYL ETHANOLAMINES, PHARMACEUTICAL COMPOSITIONS CONTAINING THEM, AND THEIR USES

[75] Inventors: Kouji Hayashi, Suita; Masahisa Hashimoto, Toyonaka; Kiyoshi Nakamura, Suita; Masanao Shimizu, Kobe; Naonobu Hatano, Takaishi; Kunihiko Takeyama, Kashihara, all of Japan

[73] Assignee: Dainippon Pharmaceutical Co., Ltd., Osaka, Japan

[22] Filed: Dec. 30, 1974

[21] Appl. No.: 537,601

[30] Foreign Application Priority Data
Jan. 12, 1974 Japan.................................. 49-6774
Dec. 5, 1974 Japan.............................. 49-140274

[52] U.S. Cl................................ 424/211; 260/403; 260/944
[51] Int. Cl.²...................... C07F 9/09; A01N 9/36
[58] Field of Search ............. 260/944, 403; 424/211

[56] References Cited
UNITED STATES PATENTS
3,577,446    5/1971    Rakhit ................................ 260/403

Primary Examiner—Anton H. Sutto
Attorney, Agent, or Firm—Sherman & Shalloway

[57] ABSTRACT

New ω-(N-acylamino)alkylphosphoryl ethanolamines and their pharmaceutically acceptable acid addition salts have superior renin-inhibitory activities, antihypertensive activities and cholesterol-lowering activities. The ω-(N-acylamino)alkylphosphoryl ethanolamines are prepared by (1) reacting an ω-(N-acylamino) alkanol with a 2-(N-substituted amino)ethyl phosphate or its derivative, hydrolyzing the resulting product or splitting off the phosphoric acid-protective group of the resulting product thereby to form an ω-(N-acylamino) alkyl 2-(N-substituted amino) ethyl phosphate, and splitting off the amino-protective groups of the resulting phosphate, or (2) reacting an ω-(N-acylamino) alkanol with a phosphorus oxyhalide, reacting the resulting ω-(N-acylamino)alkyl dichlorophosphate with a 2-(N-substituted amino) ethanol, hydrolyzing the reaction product to form an ω-(N-acylamino) alkyl 2-(N-substituted)ethyl phosphate, and splitting off the amino-protective groups of said phosphate.

24 Claims, No Drawings

ω-(N-ACYLAMINO)ALKYLPHOSPHORYL ETHANOLAMINES, PHARMACEUTICAL COMPOSITIONS CONTAINING THEM, AND THEIR USES

This invention relates to ω-(N-acylamino)alkylphosphoryl ethanolamines and their pharmaceutically acceptable acid addition salts, a process for preparing them, pharmaceutical compositions containing them, and to a method for treating hypertension using such compounds or compositions.

More specifically, this invention relates to ω-(N-acylamino)alkylphosphoryl ethanolamines of the formula

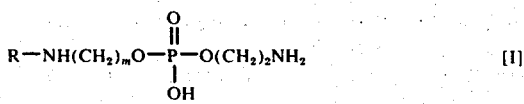

wherein R is an octadeca-9,12-dienoyl, octadeca-9,12,15-trienoyl, 4-(4'-chlorophenoxy)phenoxyacetyl or α-[4-(4'-chlorophenoxy)phenoxy]propionyl group, and m is 2 or 3,
or their pharmaceutically acceptable acid addition salts; a process for preparing them; pharmaceutical compositions containing them; and to a method for treating hypertension using them.

It has been known that normal kidneys of animals or man have antihypertensive functions, and a great deal of effort has been made to separate a substance having antihypertensive activity from kidneys. Out of these efforts emerged S. Sen et al. work which resulted in a successful separation of phosphatidyl ethanolamine having antihypertensive activity and renin-inhibitory activity (Biochemistry, Vol. 6, No. 6, p. 1572, 1967 and American Journal of Physiology, Vol. 214, No. 2, p. 337, 1968). Based on this result, further investigations were made to synthesize phosphatidyl ethanolamines having antihypertensive activity, and so far phosphatidyl ethanolamines containing only polyunsaturated fatty acid groups (containing at least 3 double bonds and 18 to 20 carbon atoms) as fatty acid groups have been reported (see U.S. Pat. No. 3,577,446).

We extensively studied the relation between the structure and activity of phosphatidyl ethanolamines in reference to their fatty acid groups (saturated and unsaturated fatty acids) and to their optical isomerism, and found that 2,3-diacyl-sn-glycero-1-phosphoryl ethanolamines and rac-2,3-diacyl-glycero-1-phosphoryl ethanolamines have superior antihypertensive activities and renin-inhibitory activities (in vitro) (see Folia Pharmacologica Japonica, Vol. 69, No. 6; p. 333 p. 1973).

However, we found that the above phosphatidyl ethanolamines are relatively unstable in vivo because of their ester linkages. Further studies in an attempt to remedy this defect led to the discovery that the compounds of the present invention containing amide linkages instead of the ester linkages have markedly superior renin-inhibitory activities (in vitro), antihypertensive activities, and cholesterol-lowering activities to the above phosphatidyl ethanolamines.

An object of this invention is to provide novel ω-(N-acylamino)alkylphosphoryl ethanolamines of general formula [I], and their pharmaceutically acceptable acid addition salts which have markedly superior renin-inhibitory activities, antihypertensive activities, and cholesterol-lowering activity.

Another object of this invention is to provide a process for preparing novel ω-(N-acylamino)alkylphosphoryl ethanolamines and their pharmaceutically acceptable acid addition salts.

Still another object of this invention is to provide a prophylactic or therapeutic composition for hypertension comprising as an active ingredient the above novel ω-(N-acylamino)alkylphosphoryl ethanolamines of formula [I] or their pharmaceutically acceptable acid addition salts.

A further object of this invention is to provide a method for treating hypertension using the above novel ω-(N-acylamino)alkylphosphoryl ethanolamines of general formula [I]or their pharmaceutically acceptable acid addition salts.

These and other objects of this invention will become more apparent from the following description.

According to this invention,, the ω-(N-acylamino)alkylphosphoryl ethanolamines of general formula [I] or their pharmaceutically acceptable acid addition salts can be prepared by the following two procedures.

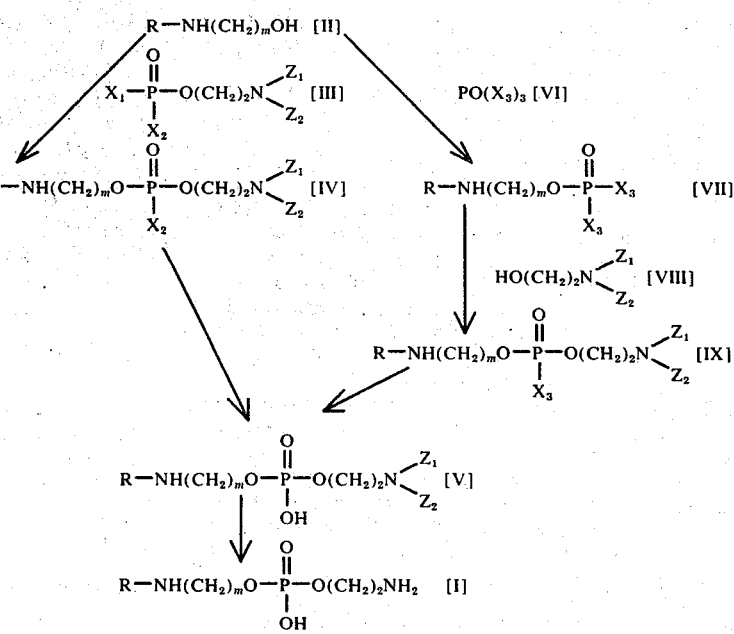

[METHOD A]

An ω-(N-acylamino)alkanol of the general formula

   [II]

wherein R and m are the same as defined above, is reacted with a 2-(N-substituted amino)ethyl phosphate or its derivative of the general formula

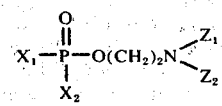   [III]

wherein $X_1$ is a halogen atom, perferably a chlorine or bromine atom, or a hydroxyl group, $X_2$ is a halogen atom, preferably a chlorine or bromine atom, a hydroxyl group or the group OY, in which Y is a protective group for a phosphoric acid group, and $Z_1$ and $Z_2$ are a protective group for an amino group, with the proviso that when $X_1$ is a halogen atom, $X_2$ is a halogen atom or the group OY, and when $X_1$ is a hydroxyl group, $X_2$ is a hydroxyl group or the group OY, to form an ω-(N-acylamino)alkyl 2-(N-substituted amino)ethyl phosphate or its derivative of the general formula

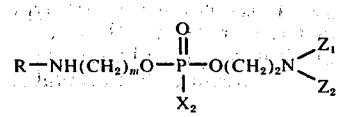   [IV]

wherein R, $X_2$, $Z_1$, $Z_2$ and m are the same as defined above.

When $X_2$ in the formula [III] is the group OY, the protective group Y for a phosphoric acid group is, for example, an aralkyl group such as a benzyl or p-nitrobenzyl group. Examples of the protective groups $Z_1$ and $Z_2$ for an amino group are trityl, β,β,β-trichloroethyoxycarbonyl, and t- butyloxycarbonyl groups. $Z_1$ and $Z_2$ may form a phthalimide group together with the adjacent nitrogen atom. Preferably, one of $Z_1$ and $Z_2$ is a hydrogen atom, and the other is the protective group.

When $X_1$ in formula [III] is a halogen atom, the reaction system becomes acidic. Hence, it is preferred to use an acid-stable protective group such as a β,β,β-trichloroethoxycarbonyl or phthalimide group.

According to the above reaction procedure, substantially stoichiometric amounts of the reactants are reacted with each other under ice cooling (about 0° to 5° C.) in an organic solvent, for example, an aliphatic halogenated hydrocarbon such as chloroform, or an aromatic hydrocarbon such as benzene. When the compound of formula [III] contains a halogen atom as $X_1$, the reaction is carried out in the presence of an acid binder, for example, a tertiary amine such as pyridine, quinoline or triethylamine at a temperature of about 0° to 20°C., and then the resulting reaction mixture is allowed to stand at room temperature (about 15° to 25° C.) for 5 to 24 hours, preferably about 10 to 14 hours, preferably in an atmosphere of an inert gas such as nitrogen. When the compound of formula [III]contains a hydroxyl group as $X_1$, the reaction is carried out in the presence of a condensing agent, for example, N,N'-dicyclohexyl carbodiimide, at room temperature (about 15° to 25° C.) for about 1 to 24 hours, preferably about 10 to 14 hours, preferably in an atmosphere of an inert gas such as nitrogen.

The resulting product is hydrolyzed when the compound of formula [IV] contains a halogen atom as $X_2$, or heated together with a metal halide when the above compound contains the group OY as $X_2$ to split off the protective group Y for a phosphoric acid group, thereby forming an ω-(N-acylamino)alkyl 2-(N-substituted amino)ethyl phosphate of the general formula

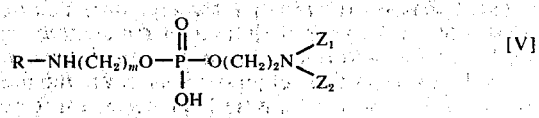   [V]

wherein R, $Z_1$, $Z_2$ and m are the same as defined above.

The above hydrolysis can be performed conveniently by adding an aqueous liquid, for example, water or a mixture of water and pyridine in an amount equimolar to or in excess of the compound of formula [IV] in which $X_2$ is a halogen atom, by a customary method to the reaction mixture obtained by the reaction of the ω-(N-acylamino)alkanol of formula [II] with the compound of formula [III] in which both $X_1$ and $X_2$ are halogen atoms, and stirring the mixture at a temperature of 0° to 30° C., preferably room temperature (about 15° to 25° C.).

Splitting off of the protective group OY can be effected by heating the above reaction mixture together with a metal halide such as sodium iodide, or an alkali metal halide such as lithium chloride in an organic solvent such as ketone (e.g., acetone or dioxane) at a temperature of about 40° to 60° C. The reaction period is not critical, but usually, it is about 1 to 7 hours, preferably about 3 to 5 hours.

When the protective groups $Z_1$ and $Z_2$ for amino groups of the compound of formula [V] are split off by a customary procedure, the final product of formula [I] can be obtained. The procedure for splitting off the amino-protective groups varies according to the type of the protective group. For example, if the protective group is a trityl group, the compound is treated with an acid such as acetic acid at about 100°C. for about 1 to 5 minutes, or at room temperature (about 15° to 25° C.) for about 15 to 24 hours. If the protective group is a trichloroethoxycarbonyl group, the product is reacted, for example, with zinc-acetic acid under ice-cooling (about 0° to 5° C.), and then subjected to a reductive cleavage reaction at room temperature (about 15° to 25° C.) for 3 to 5 hours. When the protective group is a phthalimide group, the compound is treated with hydrazine hydrate at room temperature (about 15° to 25° C.) for about 8 to 24 hours, or at an elevated temperature of about 50° to 80°C. for 1 to 2 hours. If the protective group is a t-butyloxycarbonyl group, a dry hydrogen chloride gas is blown into a chloroform solution of the compound under ice cooling (about 0° to 5°C.) for about 2 to 3 hours.

[METHOD B]

An ω-(N-acylamino)alkanol of the general formula

R—NH(CH$_2$)$_m$OH   [II]

wherein R and m are the same as defined above, is reacted with a phosphorus oxyhalide of the general formula

PO(X$_3$)$_3$   [VI]

wherein $X_3$ is a halogen atom, preferably a chlorine or bromine atom, to form an ω-(N-acylamino)alkyl dihalogenophosphate of the general formula

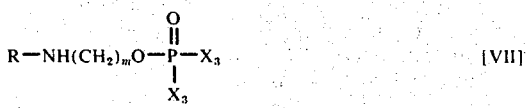
[VII]

wherein R, $X_3$ and $m$ are the same as defined above.

According to this reaction procedure, stoichiometric amounts of the reactants are preferably reacted in an anhydrous organic solvent such as an aliphatic halogenated hydrocarbon (e.g., chloroform) or an aromatic hydrocarbon (e.g., benzene) at a temperature of about 0° to 30° C., preferably under ice cooling (about 0° to 5° C.), and then allowed to stand at room temperature (about 15° to 25° C.) for about 1 to 12 hours, preferably about 3 to 5 hours.

The resulting compound of formula [VII] is reacted with a 2-(N-substituted amino) ethanol expressed by the following general formula

[VIII]

wherein $Z_1$ and $Z_2$ are the same as defined above, to form an ω-(N-acylamino)alkyl 2-(N-substituted amino)ethyl halogenophosphate expressed by the following formula

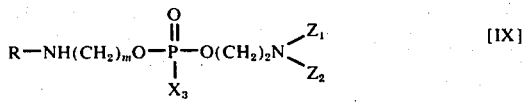
[IX]

wherein R, $X_3$, $Z_1$, $Z_2$ and $m$ are the same as defined above.

Preferably, the reaction between the compound of formula [VII] and the compound of formula [VIII] is carried out in an anhydrous organic solvent, for example, an aliphatic halogenated hydrocarbon such as chloroform or an aromatic hydrocarbon such as benzene in the presence of an acid binder, for example, a tertiary amine such as pyridine, quinoline or triethylamine at a temperature of about 0° to 30° C., preferably under ice cooling (about 0° to 5°C.), and then allowing them to stand at room temperature (about 15° to 25°C.) for about 1 to 24 hours, preferably about 5 to 12 hours.

The subsequent hydrolysis of the compound of formula [IX] to the compound of formula [V] can be performed in the same way as in Method A described above.

When the amino-protective groups of the resulting compound of formula [V] are split off in the same way as in Method A, there can be obtained a final compound of formula [I].

The compounds of formula [I] can be isolated, and purified in a customary manner.

The compound of formula [II] used in the above Methods A and B can be obtained, for example, by the following procedures.

1. When R in formula [II] is an octadeca-9,12-dienoyl or octadeca-9,12,15-trienoyl group:
An acid of the general formula

R—OH       [X]

wherein R is the same as defined above, or their lower alkyl ester is reacted with an ω-aminoalkanol of the general formula

[XI]

wherein $m$ is the same as defined above, at an elevated temperature in a stream of nitrogen, and the reaction product is purified in a customary manner to form the compound of formula [II].

2. When R in formula [II] is a 4-(4'-chlorophenoxy)phenoxyacetyl or α-[4-(4'-chlorophenoxy)phenoxy]propionyl group:

4-(4'-chlorophenoxy)phenol is reacted with an ester of the general formula

[XII]

wherein Hal is a halogen atom, A is a methylene or methylmethylene group, and W is a lower alkyl group, in an organic solvent such as methyl ethyl ketone in the presence of an inorganic or organic base (for example, potassium carbonate or sodium carbonate) at an elevated temperature to form an ester of the general formula

[XIII]

wherein A and W are the same as defined above.

The resulting ester is reacted with an ω-aminoalkanol of the general formula

[XIV]

wherein $m$ is the same as defined above, at an elevated temperature either in the absence of a solvent or in the presence of an anhydrous inert solvent such as toluene to form the compound of formula [II].

The compounds in accordance with this invention are obtained in a free form in accordance with the Method A or B. They can be converted to their pharmaceutically acceptable acid addition salts by reaction in a customary manner with an inorganic acid such as hydrochloric acid, hydrobromic acid, hydriodic acid, sulfuric acid or nitric acid or an organic acid such as malonic acid, fumaric acid, maleic acid, oxalic acid, tartaric acid, citric acid, malic acid or lactic acid.

Preferred compounds of this invention are, for example, as follows:

3-(octadeca-9,12-15-trienonylamino)propylphosphoryl ethanolamine;

3-(octadeca-9,12-dienoylamino)propylphosphoryl ethanolamine,

2-[4-(4'-chlorophenoxy)phenoxyacetylamino]ethylphosphoryl ethanolamine; and

2- α-[4-(4'-chlorophenoxy)phenoxy]propionylamino ethylphosphoryl ethanolamine.

The ω-(N-acylamino)alkylphosphoryl ethanolamines and their pharmaceutically acceptable acid addition salts in accordance with this invention have markedly superior renin-inhibitory activities, antihypertensive activities, and cholesterol-lowering activities to the known phosphatidyl ethanolamines, as will be demonstrated in Example 18 of this application.

As regards the renin-inhibitory activity, J. H. Laragh (Circulation, Vol. 44, p. 971, 1971 and Am. J. Med., Vol. 55, p. 261, 1973), H. R. Brunner (Am. J. Med., Vol. 55, p. 295, 1973) and Y. Kanebo (Jap. Cir. J., Vol. 36, p. 995, 1972) reported that as a result of investigations into the relation of the occurrence of hypertensive cardiovascular diseases and the renin activity in blood, it was found that when the amount of renin in blood is maintained at a low level, the rate of occurrence of cerebral apolexi and myocardial infarction is low and prognosis is also good. Accordingly, it is expected that the compounds of this invention having renin-inhibitory activities will be useful as prophylactic or therapeutic pharmaceuticals for cerebral apolexi and myocardial infarction.

Furthermore, the compounds of this invention have markedly superior antihypertensive activities to the conventional phosphatidyl ethanolamines as will be shown in Example 18, and by continuous administration, the effects will become more remarkable. The compounds of this invention, moreover, have low toxicity as represented by an acute toxicity (p.o.) of $LD_{50} > 2,000$ mg/Kg(mouse) or $LD_{50} > 1,000$ mg/Kg(rat). Furthermore, the compounds of this invention are more soluble in water than the known phosphatidyl ethanolamines, and can be advantageously formulated.

The ω-(N-acylamino)alkylphosphoryl ethanolamines and their pharmaceutically acceptable acid addition salts can be formulated into a pharmaceutical composition (for example, powders, granules, microcapsules, or emulsions) by mixing with conventional pharmaceutical carriers. The pharmaceutical composition can be converted by a customary method into final administrable forms, for example, tablets, capsules, powders, or liquids such as solutions, emulsions, suspensions or syrups for oral administration, and if necessary, it may be formulated into a sterilized aqueous solution which is buffered or made isotonic, for parenteral administration. Alternatively, the tablets may be coated by a customary method to prepare longlasting or slow-releasing tablets.

In the production of the above composition or preparation containing the compounds of this invention, various non-toxic pharmaceutical carriers compatible with the compounds of this invention which are well known in the art can be used. Examples of such carriers are excipients such as microcrystalline cellulose, lactose, starch or the like, lubricants such as silicic anhydride, magnesium stearate, talc, sodium laurylsulfate or the like, and binders such as starch paste, lactose, mannitol, magnesium trisilicate, gelatin or the like. In the liquid composition or preparation, a conventional liquid carrier such as water can also be used.

In oral administration, the daily dosage of the compound of this invention is about 2 to 30 mg, preferably about 5 to 20 mg, and more preferably about 8 to 12 mg, per kilogram of the body weight. In parenteral administration, the daily dosage of the compound of this invention is about 0.2 to 3 mg, preferably about 0.5 to 2 mg, more preferably about 0.8 to 1.2 mg, per kilogram of the body weight. Thus, the pharmaceutical composition or preparation of this invention can contain the compound of this invention in a daily dosage unit of about 10 to 1500 mg, preferably about 25 to 1,000 mg, more preferably about 40 to 600 mg. Especially in oral administration, it contains the compounds in a daily dosage unit of about 100 to 1500 mg, preferably about 250 to 1000 mg, more preferably about 400 to 600 mg. In the case of parenteral administration, it contains the compounds of this invention in a daily dosage unit of about 10 to 150 mg, preferably about 25 to 100 mg, more preferably about 40 to 60 mg. The total dosage may be administered in smaller portions three or four times a day as determined by the attending physician.

According to this invention, hypertension can be prevented or treated by administering the ω-(N-acylamino)alkylphosphoryl ethanolamine and its pharmaceutically acceptable acid addition salt or the composition or preparation containing it orally or parenterally (for example, intravenously, intramuscularly, or hypodermically) to the patients in the dosages specified above.

The following Examples illustrate the present invention in greater detail.

REFERENTIAL EXAMPLE 1

11.0 g (40 millimols) of octadeca-9,12,15-trienoic acid (linoleic acid) and 3.7 g (60 millimols) of ethenolamine were reacted in a stream of nitrogen at 160°C. for 2 hours. The resulting reaction mixture was cooled, and purified by silica-chromatography (chloroform-methanol in a volume ratio of 95:5) to afford 12.7 g of oily octadeca-9,12,15-trienoylaminoethanol in a quantitative yield.

Elemental analysis values for $C_{20}H_{35}NO_2$:-
| | | | |
|---|---|---|---|
| Calculated (%): | C 74.71 | H 10.97 | N 4.36 |
| Found (%): | C 74.50 | H 11.21 | N 4.48 |

IR (film):
νC=O (amide I)          1640 cm$^{-1}$
δNH + νCN (amide II)    1540 cm$^{-1}$ In the same manner as above, 13.2 g of 3-(octadeca-9,12,15-trienoylamino)propanol was obtained in a quantitative yield from 11.0 g (40 millimols) of octadeca-9,12,15-trienoic acid (linoleic acid) and 4.5 g (60 millimols) of 3-aminopropanol.

REFERENTIAL EXAMPLE 2

5.0 g (45 millimols) of methyl chloroacetate was added to a mixture consisting of 6.6 g (30 millimols) of 4-(4'-chlorophenoxy)phenol, 4.14 g (30 millimols) of anhydrous potassium carbonate and 60 ml. of methyl ethyl ketone, and they were reacted under reflux with stirring for 7 hours. The reaction mixture obtained was cooled, and filtered. The filtrate was concentrated at reduced pressure, and purified by silica-chromatography (chloroform) to afford 8.1 g of oil methyl 4-(4'-chlorophenoxy)phenoxyacetate in a yield of 92%.

The resulting substance (8.1 g = 28 millimols) and 2.3 g (33 millimols) of ethanolamine were reacted with stirring for 2 hours over an oil bath (about 160° C.) while removing the by-product water. The reaction mixture obtained was cooled, and purified by silica-chromatography (chloroform/methanol in a volume ratio of 95:5) to afford 8.5 g of crystals of 2-[4-(4'-chlorophenoxy)phenoxyacetylamino]ethanol in a yield of 95% having a melting point of 84° to 85° C. (recrystallized from acetone-cyclohexane).

Elemental analysis values for $C_{16}H_{16}ClNO_4$: Calculated (%): C, 59.72; H, 5.01; N, 4.35; Cl, 11.02. Found (%): C, 59.69, H, 4.86; N, 4.45; Cl, 10.98.

REFERENTIAL EXAMPLE 3

20 g (150 millimols) of methyl α-bromopropionate was added to a mixture consisting of 22.1 g (100 millimols) of 4-(4'-chlorophenoxy)phenol, 13.8 g (100 millimols) of anhydrous potassium carbonate and 220 ml. of methyl ethyl ketone, and they were reacted under reflux with stirring for 6 hours. The reaction mixture obtained was cooled, and filtered. The filtrate was concentrated at reduced pressure, and purified with alumina-chromatography (benzene) to afford 25 g of methyl α-[4-(4'-chlorophenoxy)phenoxy]propionate in a yield of 81%.

25 g (80 millimols) of the resulting product and 7.5 g (110 millimols) of ethanolamine were treated in the same way as in Referential Example 2 to afford 25 g of 2- α-[4-(4'-chlorophenoxy)phenoxy]propionylamino -ethanol having a melting point of 87° to 88° C. (recrystallized from acetone-ether) in a yield of 92%.

Elemental analysis values for $C_{17}H_{18}ClNO_4$: Calculated (%): C, 60.81; H, 5.40; N, 4.17; Cl, 10.56. Found (%): C, 60.88; H, 5.30; N, 4.13; Cl, 10.44.

REFERENTIAL EXAMPLE 4

6.6 g (30 millimols) of 4-(4'-chlorophenoxy)phenol, 4.14 g (30 millimols) of potassium carbonate, 60 ml. of methyl ethyl ketone and 5.0 g (45 millimols) of methyl chloroacetate were treated in the same way as in Referential Example 2 to afford 8.1 g of oily methyl 4-(4'-chlorophenoxy)phenoxyacetate in a yield of 92%.

8.1 g (28 millimols) of the product obtained above and 3.3 g (44 millimols) of 3-aminopropanol were treated in the same way as in Referential Example 2 to afford 9.0 g of 3-[4-(4'-chlorophenoxy)phenoxyacetylamino]propanol having a melting point of 74° to 75°C. (recrystallized from acetone-cyclohexane) in a yield of 92%.

Elemental analysis values for $C_{17}C_{18}ClNO_4$: Calculated (%): C, 60.81; H, 5.40; N, 4.17; Cl, 10.56. Found (%): C, 60.66; H, 5.22; N, 4.07; Cl, 10.57.

REFERENTIAL EXAMPLE 5

6.63 g (30 millimols) of 4-(4'-chlorophenoxy)-phenol, 4.14 g (30 millimols) of anhydrous potassium carbonate, 60 ml. of methyl ethyl ketone and 5.5 g (40 millimols) of methyl α-bromopropionate were treated in the same way as in Referential Example 2 to afford 8.3 g of oily methyl α-[4-(4'-chlorophenoxyl)phenoxy]propionate in a yield of 90%.

8.3 g of (27 millimols) of the resulting product and 3.0 g (40 millimols) of 3-aminopropanol were treated in the same way as in Referential Example 2 to afford 9.0 g of 3- α-[4-(4'-chlorophenoxy)phenoxy]propionylamino propanol having a melting point of 55° to 56° C. (recrystallized from ether-cyclohexane) in a yield of 95%.

Elemental analysis values for $C_{18}H_{20}ClNO_4$: Calculated (%): C, 61.81; H, 5.76; N, 4.01; Cl, 10.13. Found (%): C, 61.79; H, 5.69; N, 3.92; Cl, 9.97.

EXAMPLE 1

To a stirred solution of 23 g (70 millimols) of octadeca-9,12-dienoylaminoethanol in 60 ml. of chloroform and 30 ml. of anhydrous pyridine, a solution of 25 g (80 millimols) of 2-(N-phthalimido)ethyl dichlorophosphate in 60 ml. of chloroform was added dropwise while cooling it. After maintaining the mixture cold for 30 minutes, the temperature was returned to room temperature, and the mixture was stirred for 5 hours, followed by standing overnight in a stream of nitrogen. The reaction mixture obtained was diluted with chloroform, and then shaken three times with a 0.1M potassium chloride solution. The chloroform layer was treated with anhydrous sodium sulfate, and concentrated at reduced pressure to form a crude oily substance. The crude substance was purified by silica-chromatography (chloroform-methanol in a volume ratio of 95:5) to afford 31 g of oily 2-(octadeca-9,12-dienoylamino)ethyl 2-(N-phthalimido) ethyl phosphate in a yield of 65%.

5.8 g (10 millimols) of the resulting oily substance was dissolved in 85 ml. of ethanol, and 0.6 ml (12 millimols) of 100% hydrazine hydrate was added under ice cooling. THe temperature was returned to room temperature, and the mixture was refluxed for 1.5 hours in a stream of nitrogen. The mixture was cooled, and filtered. The filtrate was concentrated at reduced pressure, treated with chloroform, purified by silica-chromatography (chloroform/methanol in a volume ratio of 1:1), and crystallized from acetone-ether to afford 2.3 g of powdery 2-(octadeca-9,12-dienoylamino)ethylphosphoryl ethanolamine in a yield of 63%.

Elemental analysis values for $C_{22}H_{43}N_2O_5P$: Calculated (%): C, 59.17; H, 9.71; N, 6.28; P, 6.94. Found (%): C, 58.40; H, 9.72; N, 6.31; P, 6.40.

| | |
|---|---|
| νC=O (amide) | 1640 cm⁻¹ |
| δNH + νCN (amide) | 1550 cm⁻¹ |
| νP=O (phosphate) | 1210 cm⁻¹ |
| νP—O—C (phosphate) | 1070, 995 cm⁻¹ |

TLC (silica gel, chloroform/methanol/water =65/25/4):

Rf = 0.19

20 ml of methanol (containing 5% dry hydrogen chloride) was added to 0.45 g (1 millimol) of the above product to make a complete solution. The solution was concentrated at reduced pressure, and upon adding acetone, a precipitate was obtained. The precipitate was filtered, washed with ether, and dried at room temperature and reduced pressure to afford 0.48 g of a hydrochloride of the above product as a waxy substance in a yield of 97%.

Elemental analysis values for $C_{22}H_{44}ClN_2O_5P$: Calculated (%): C, 54.71; H, 9.18; N, 5.80; P, 6.41; Cl, 7.34. Found (%): C, 54.01; H, 9.38; N, 5.72; P, 6.20; Cl, 7.58.

| IR (KBr disk) | |
|---|---|
| νN⁺H (amine salt) | 2400–2600 cm⁻¹ |
| νC=O (amide) | 1630 cm⁻¹ |
| δNH + νCN (amide) | 1555 cm⁻¹ |
| νP=O (phosphate) | 1220 cm⁻¹ |
| νP—O—C (phosphate) | 980–1050 cm⁻¹ |

EXAMPLE 2

To a stirred solution of 10.5 g (32.3 millimols) of octadeca-9,12-dienoylaminoethanol in 30 ml. of chloroform and 15 ml. of anhydrous pyridine, a solution of 20.5 g (58 millimols) of 2-(N-β,β,β-trichloroethoxycarbonylamino)ethyl dichlorophosphate in 30 ml. of chloroform was added gradually while cooling it. After maintaning it cold for 30 minutes, the temperature was returned to room temperature. After stirring for 5 hours, the mixture was allowed to stand overnight in a stream of nitrogen. The mixture was diluted with chloroform, and washed three times with a 0.1 M potassium chloride solution. The chloroform layer was concentrated at reduced pressure, and purified by silica-chromatography (chloroform/methanol in a volume ratio of 95/5). The product was further purified by chromatography using Florisil (a trademark) to afford 16 g of oily 2-(octadeca-9,12-dienoylamino)ethyl 2-(N-β,β,β-trichloroethoxycarbonylamino)ethyl phosphate in a yield of 82%.

6.0 g (10 millimols) of the resulting product was dissolved in 25 ml. of 90% acetic acid and 50 ml. of ether, and 30 mg of zinc powder was added with stirring under ice cooling. The mixture was stirred at room temperature for 3 hours, and filtered. The filtrate was concentrated at reduced pressure at a temperature of less than 40°C., and purified by silica-chromatography (chloroform/methanol in a volume ratio of 1/1). The product was further purified with acetone-ether to afford 2.4 g of powdery 2-(octadeca-9,12-dienoylamino)ethylphosphoryl ethanolamine in a yield of 54%.

EXAMPLE 3

To a stirred solution of 6.7 g (20 millimols) of 3-(octadeca-9,12,15-trienoylamino)propanol in 6 ml. of chloroform and 3.5 ml. of anhydrous pyridine, a solution of 7.0 g (22.5 millimols) of 2-(N-phthalimidoethyl dichlorophosphate in 15 ml. of chloroform was gradually added while cooling it with ice. The same treatment of the mixture as in Example 1 afforded 9.4 g of oily 3-(octadeca-9,12,15-trienoylamino)propyl 2-(N-phthalimido)ethyl phosphate in a yield of 80%.

9.4 g (16.2 millimols) of the resulting product was dissolved in 120 ml. of ethanol, and 2.6 ml. of 100% hydrazine hydrate was added. The same treatment of the mixture as in Example 1 afforded 3.2 g of powdery 3-(octadeca-9,12,15-trienoylamino)propylphosphoryl ethanolamine in a yield of 44%.

Elemental analysis for $C_{23}H_{43}N_2O_5P$: Calculated (%): C, 60.24; H, 9.54; N, 6.11; P, 6.75. Found (%): C, 59.06; H, 9.79; N, 6.18; P, 6.10.

| IR (film): | |
|---|---|
| $\nu C=O$ (amide) | 1640 cm$^{-1}$ |
| $\delta NH + \nu CN$ (amide) | 1550 cm$^{-1}$ |
| $\nu P=O$ (phosphate) | 1210 cm$^{-1}$ |
| $\nu P-O-C$ (phosphate) | 1075, 1000 cm$^{-1}$ |

TLC (silica gel: chloroform/methanol/water=65/25/4):

Rf=0.20

EXAMPLE 4

To a stirred solution of 11.5 g (34 millimols) of 3-(octadeca-19,12-dienoylamino)propanol in 30 ml. of chloroform and 7 ml. of anhydrous pyridine, a solution of 14 g (45 millimols) of 2-(N-phthalimido)ethyl dichlorophosphate in 30 ml. of chloroform was gradually added dropwise while cooling it. The same treatment of the mixture as in Example 1 afforded 17 g of oily 3-(octadeca-9,12-dienoylamino)propyl 2-(N-phthalimido)ethyl phosphate in a yield of 85%.

8.5 g (14.7 millimols) of the resulting product was dissolved in 100 ml. of ethanol, and 1.7 ml. of 100% hydrazine hydrate was added. The same treatment of the mixture as in Example 1 afforded 3.4 g of powdery 3-(octadeca-9,12-dienoylamino)propylphosphoryl ethanolamine in a yield of 54%.

Elemental analysis values for $C_{23}H_{45}N_2O_5P$: Calculated (%): C, 59.98; H, 9.85; N, 6.08; P, 6.70. Found (%): C, 59,37; H, 9.67; N, 6.09; P, 6.36.

| IR (film): | |
|---|---|
| $\nu C=O$ (amide) | 1640 cm$^{-1}$ |
| $\delta NH + \nu CN$ (amide) | 1545 cm$^{-1}$ |
| $\nu P=O$ (phosphate) | 1215 cm$^{-1}$ |
| $\nu P-O-C$ (phosphate) | 1070, 995 cm$^{-1}$ |

TLC (silica gel; chloroform/methanol/water=65/25/4):

Rf=0.20

EXAMPLE 5

To a stirred solution of 1.63 g (5 millimols) of octadeca-9,12-dienoylaminoethanol in 10 ml. of chloroform and 1.5 g (10 millimols) of triethylamine, a solution of 1.9 g (5 millimols) of 2-(N-phthalimido)ethyl benzyl chlorophosphate in 10 ml. of chloroform was gradually added dropwise while cooling it. The mixture was stirred at room temperature for 2 hours, and allowed to stand overnight in a stream of nitrogen. Then, the mixture obtained was diluted with chloroform, and shaken three times with a 0.1 M potassium chloride solution. The chloroform layer was concentrated at reduced pressure, and treated with neutral alumina (chloroform) to afford 2.1 g of oily 2-(octadeca-9,12-dienoylamino)ethyl 2-(N-phthalimido)ethyl benzyl phosphate in a yield of 68%.

1.1 g (1.6 millimols) of the resulting product and 0.36 g (2.4 millimols) of anhydrous sodium iodide were dissolved in 30 ml. of anhydrous acetone, and the mixture was refluxed with stirring for 3.5 hours in a stream of nitrogen. The mixture was cooled to room temperature, and after adding 4 ml. of triethylamine, allowed to stand overnight. The resulting mixture was concentrated at reduced pressure, and treated with neutral alumina to afford 1.0 g of oily 2-(octadeca-9,12-dienoylamino)ethyl 2-(N-phthalimido)ethyl phosphate in a quantitative yield.

1.0 g (1.7 millimols) of the resulting product was dissolved in ethanol in the same way as in Example 1, and treated with 100% hydrazine hydrate to afford 0.4 g of 2-(octaceca-9,12-dienoylamino)ethylphosphoryl ethanolamine in a yield of 50%.

EXAMPLE 6

To a stirred mixture of 0.66 g (2 millimols) of octadeca-9,12-dienoylaminoethanol and 0.56 g (2 millimols) of 2-(N-phthalimido)ethyl phosphate in 20 ml. of anhydrous pyridine, 0.9 g (4.5 millimols) of N,N'-dicyclohexylcarbodimide was added. After stirring the mixture for 30 minutes, it was allowed to stand overnight at room temperature in a stream of nitrogen. The precipitate was separated by filtration, and the filtrate was concentrated at reduced pressure. It was then purified by silica-chromatography (chloroform/methanol in a volume ratio of 9/1) to afford 0.8 g of oily 2-(octadeca-9,12-dienoylamino)ethyl 2-(N-phthalimido)ethyl phosphate in a yield of 69%.

0.8 g (1.4 millimols) of the resulting product was dissolved in ethanol in the same way as in Example 1, and treated with 100% hydrazine hydrate to afford 0.30 g of 2-(octadeca-9,12-dienoylamino)ethylphosphoryl ethanolamine in a yield of 50%.

EXAMPLE 7

To a stirred solution of 3.22 g (10 millimols) of octadeca-9,12,15-trienoylaminoethanol and 1.3 g (10 millimols) of anhydrous quinoline in 5 ml. of chloroform, a solution of 1.54 g (10 millimols) of distilled phosphorus oxychloride in 5 ml. of chloroform was gradually added dropwise while cooling it. After ice cooling for 30 minutes, the mixture was continuously stirred at room temperature for 3 hours in a stream of nitrogen. Then, a solution of 1.91 g (10 millimols) of 2-(N-phthalimido)ethanol and 2 ml. of anhydrous pyridine in 20 ml. of chloroform was gradually added dropwise to the mixture while cooling it. The temperature was returned to room temperature 30 minutes later, and the reaction was continued overnight. The reaction mixture obtained was diluted with a suitable amount of chloroform, shaken three times with a 0.1M potassium chloride, and washed. The chloroform layer was treated with anhydrous sodium sulfate, and concentrated at reduced pressure. It was then purified by silica-chromatography (chloroform/methanol in a volume ratio of 95:5) to afford 4.3 g of oily 2-(octadeca-9,12,15-trienoylamino)ethyl 2-(N-phthalimido)ethyl phosphate in a yield of 76%.

4.3 g (7.4 millimols) of the resulting product was dissolved in 80 ml. of ethanol, and 1.5 ml. of 100% hydrazine hydrate was added. The mixture was refluxed for 1.5 hours in a stream of nitrogen. The resulting precipitate was removed under cooling, and concentrated at reduced pressure. It was treated with chloroform, and purified by silica-chromatography and further with acetone-ether to afford 0.43 g of powdery 2-(octadeca-9,12,15-trienoylamino)ethylphosphoryl ethanolamine in a yield of 10%.

Elemental analysis values for $C_{22}H_{41}N_2O_5P$: Calculated (%): C, 59.44; H, 9.30; N, 6.30; P, 6.96. Found (%): C, 60.03; H, 9.76; N, 6.63; P, 6.74.

| IR (film): | |
|---|---|
| $\nu C=O$ (amide) | 1640 cm$^{-1}$ |
| $\delta NH + \nu CN$ (amide) | 1545 cm$^{-1}$ |
| $\nu P=O$ (phosphate) | 1215 cm$^{-1}$ |
| $\nu P-O-C$ (phosphate) | 1070, 995 cm$^{-1}$ |

TLC (silica gel; chloroform/methanol/water=65/25/4):

Rf = 0.19

EXAMPLE 8

To a stirred solution of 3.22 g (10 millimols) of octadeca-9,12,15-trienoylaminoethanol and 1.3 g (10 millimols) of anhydrous quinoline in 5 ml. of chloroform, a solution of 1.54 g (10 millimols) of distilled phosphorus oxychloride in 5 ml. of chloroform was gradually added dropwise while cooling it. After ice cooling for 30 minutes, the mixture was continuously stirred in a stream of nitrogen at room temperature for 3 hours, and again with stirring, a solution of 3.07 g (10 millimols) of 2-tritylaminoethanol and 2 ml. of anhydrous pyridine in 20 ml. of chloroform was gradually added to the mixture while cooling it with ice. 30 minutes later, the temperature was returned to room temperature, and the reaction was carried out overnight with stirring. The resulting reaction mixture was diluted with a suitable amount of chloroform, shaken three times with a 0.1M potassium chloride solution, and washed with water. The chloroform layer was treated with anhydrous sodium sulfate, and concentrated at reduced pressure. It was purified by silica-chromatography (chloroform/methanol in a volume ratio of 95/5) to afford 4.8 g of oily 2-(octadeca-9,12,15-trienoylamino)ethyl 2-(triethylamino)ethyl phosphate in a yield of 70%.

4.8 g (7.0 millimols) of the resulting product was dissolved in 20 ml. of acetic acid, and 2 ml. of water was added. The solution was treated in a stream of nitrogen at 100°C. for 3 minutes, cooled, concentrated at reduced pressure, and then treated in the same way as in Example 1 to afford 0.90 g of 2-(octadeca-9,12,15-trienoylamino)ethyl phosphoryl ethanolamine in a yield of 20%.

EXAMPLE 9

To a stirred solution of 7.25 g (22 millimols) of 2-[4-(4'-chlorophenoxy)phenoxyacetylamino]ethanol in 9 ml. of anhydrous pyridine and 35 ml. of chloroform, a solution of 9.5 g (29 millimols) of 2-(N-phthalimido)ethyl dichlorophosphate in 25 ml. of chloroform was gradually added dropwise while cooling it with ice. 30 minutes later, the temperature was returned to room temperature, and the mixture was stirred for 5 hours, and allowed to stand overnight. It was diluted with chloroform, and shaken three times with a 0.1M potassium chloride solution. The chloroform layer was dehydrated, and concentrated at reduced pressure to afford 11 g of 2-[4-(4'-chlorophenoxy)phenoxyacetylamino]ethyl 2-(N-phthalimido)ethyl phosphate as a crude oily substance in a yield of 85%.

To 11 g (19 millimols) of the resulting product were added 130 ml. of ethanol and 0.9 ml. of 100% hydrazine hydrate. The mixture was refluxed for 1.5 hours with stirring, cooled, and filtered. The filtrate was concentrated at reduced pressure, and purified by silica-chromatography (chloroform/methanol in a volume ratio of 1:1). The resulting crude product was further treated with acetone-ether to afford 3.8 g of 2-[4-(4'-chlorophenoxy)phenoxyacetylamino]ethylphosphoryl ethanolamine having a melting point of 178° to 180°C. in a yield of 40%.

Elemental analysis for $C_{18}H_{22}ClN_2O_7P$: Calculated (%): C, 48.60; H, 4.99; N, 6.30; P, 6.96; Cl, 7.97. Found: (%): C, 48.34; H, 5.14; N, 6.28; P, 6.58; Cl, 7.98.

IR (KBr disk):-

| | |
|---|---|
| $\nu$C=O (amide) | 1655 cm$^{-1}$ |
| $\delta$NH + $\nu$CN (amide) | 1550 cm$^{-1}$ |
| $\nu$P=O (phosphate) | 1210 cm$^{-1}$ |
| $\nu$P—O—C (phosphate) | 1070, 1000 cm$^-$ |

TLC (silica gel; chloroform/methanol/water = 95/35/6):

Rf = 0.41

0.45 g (1 millimol) of the resulting product was dissolved completely in 20 ml. of methanol (containing 5% of dry hydrogen chloride). The solution was concentrated at reduced pressure, and acetone was added to form a precipitate. The precipitate was filtered, washed with ether, and dried at room temperature under reduced pressure to afford 0.46 g in hydrochloride form of the above product in a yield of 96% having a melting point of 121° to 123°C.

Elemental analysis values for $C_{18}H_{23}Cl_2N_2O_7P$: Calculated (%): C, 44.92; H, 4.82; N, 5.82; P, 6.43; Cl, 14.79. Found (%): C, 44.62; H, 4.62; N, 5.85; P, 6.29; Cl, 14.69.

IR (KBr disk):-

| | |
|---|---|
| $\nu$N$^+$H (amine salt) | 2450–2600 cm$^{-1}$ |
| $\nu$C=O (amide) | 1645 cm$^{-1}$ |
| $\delta$NH + $\nu$CN (amide) | 1545 cm$^{-1}$ |
| $\nu$P=O (phosphate) | 1215 cm$^{-1}$ |
| $\nu$P—O—C (phosphate) | 1000–1050 cm$^{-1}$ |

EXAMPLE 10

To a stirred solution of 25 g (75 millimols) of 2-α-[4-(4'-chlorophenoxy)phenoxy]propionylamino ethanol in 35 ml of anhydrous pyridine and 50 ml. of chloroform, a solution of 31 g (101 millimols) of 2-(N-phthalimido)ethyl dichlorophosphate in 100 ml. of chloroform was gradually added dropwise under cooling. The mixture was treated in the same way as in Example 9 to afford 37 g of 2- α-[4-(4'-chlorophenoxy)phenoxy]propionylamino ethyl 2-(N-phthalimido)ethyl phosphate as a crude oily substance in a yield of 85%.

300 ml. of ethanol and 3 ml. of 100% hydrazine hydrate were added to 37 g (63 millimols) of the product obtained, and the mixture was treated in the same way as in Example 9 to afford 11.6 g of 2- α-[4-(4'-chlorophenoxy)phenoxy]propionylamino ethylphosphoryl ethanolamine having a melting point of 156° to 158° C. in a yield of 40%.

Elemental analysis values for $C_{19}H_{24}ClN_2O_7P$: Calculated (%): C, 49.75; H, 5.27; N, 6.11; P, 6.75; Cl, 7.73. Found (%): C, 48.76; H, 5.27; N, 6.33; P, 6.42; Cl, 7.66.

IR (KBr disk):-

| | |
|---|---|
| $\nu$C=O (amide) | 1655 cm$^{-1}$ |
| $\delta$NH + $\nu$CN (amide) | 1540 cm$^{-1}$ |
| $\nu$P=O (phosphate) | 1210 cm$^{-1}$ |
| $\nu$P—O—C (phosphate) | 1070, 1020 cm$^{-1}$ |

TLC (silica gel; chloroform/methanol/water=95/35/6):

Rf = 0.43

EXAMPLE 11

To a stirred solution of 9.0 g (27 millimols) of 3-[4-(4'-chlorophenoxy)phenoxyacetylamino]propanol in 8 ml. of anhydrous pyridine and 30 ml. of chloroform, a solution of 12 g (39 millimols) of 2-(N-phthalimide)ethyl dichlorophosphate in 40 ml. of chloroform was gradually added dropwise while cooling it with ice. The mixture was then treated in the same way as in Example 9 to afford 13.1 g of 3-[4-(4'-chlorophenoxy) phenoxyacetylamino]propyl 2-(N-phthalimido)ethyl phosphate as a crude oily substance in a yield of 93%.

80 ml. of ethanol and 1.5 ml. of 100% hydrazine hydrate were added to 13.1 g (23 millimols) of the resulting product, and the mixture was treated in the same way as in Example 9 to afford 3.5 g of 3-[4-(4'-chlorophenoxy)phenoxyacetylamino]propylphosphoryl ethanolamine having a melting point of 197° to 199° C. in a yield of 97%.

Elemental analysis values for $C_{19}H_{24}C.N_2O_7P$: Calculated (%): C, 49.74; H, 5.27; N, 6.11; P, 6.75; Cl, 7.73. Found (%): C, 49.18; H, 5.48; N, 6.42; P, 6.46; Cl, 7.48.

| IR (KBr disk):- | |
|---|---|
| $\nu$C=O (amide) | 1660 cm$^{-1}$ |
| $\delta$NH + $\nu$CN (amide) | 1545 cm$^{-1}$ |
| $\nu$P=O (phosphate) | 1215 cm$^{-1}$ |
| $\nu$P—O—C (phosphate) | 1075, 1000 cm$^{-1}$ |

TLC (silica gel; chloroform/methanol/water=95/35/6):

Rf = 0.41

EXAMAPLE 12

To a stirred solution of 9.0 g (26 millimols) of 3- α-[4-(4'-chlorophenoxy)phenoxy]propionylaminopropanol in 9 ml. of anhydrous pyridine and 50 ml. of chloroform, a solution of 10.5 g (34 millimols) of 2-(N-phthalimide)ethyl dichlorophosphate in 40 ml. of chloroform was gradually added dropwise while cooling it with ice. The resulting mixture was treated in the same way as in Example 9 to afford 12.9 g of 3- α-[4-(4'-chlorophenoxy)phenoxy]propionylamino propyl 2-(N-phthalamido)ethyl phosphate as a crude oily substance in a yield of 83%.

150 ml. of ethanol and 1.0 ml. of 100% hydrazine hydrate were added to 12.9 g (22 millimols) of the resulting product, and the mixture was treated in the same way as in Example 9 to afford 4.1 g of 3- α-[4-(4'-chlorophenoxy)phenoxy]propionylamino propylphosphoryl ethanolamine having a melting point of 162° to 164°C. in a yield of 40%.

Elemental analysis values for $C_{20}H_{26}ClN_2O_7P$: Calculated (%): C, 50.80; H, 5.54; N, 5.93; P, 6.55; Cl, 7.50. Found (%): C, 50.12; H, 5.81; N, 6.12; P, 6.48; Cl, 7.36.

| IR (KBr disk):- | |
|---|---|
| $\nu$C=O (amide) | 1655 cm$^{-1}$ |
| $\delta$NH + $\nu$CN (amide) | 1500 cm$^-$ |
| $\nu$P=O (phosphate) | 1210 cm$^{-1}$ |
| $\nu$P—O—C (phosphate) | 1070, 1010 cm$^{-1}$ |

TLC (Silica gel; chloroform/methanol/water=95/35/6): Rf = 0.42

EXAMPLE 13

0.67 g (2 millimols) of 2- α-[4-(4'-chlorophenoxy)-phenoxy]propionylamino ethanol and 0.56 g (2 millimols) of 2-(N-phthalimido)ethyl phosphate were dissolved in 20 ml. of anhydrous pyridine with stirring, and 0.9 g (4.5 millimols) of N,N'-dicyclohexylcarbodiimide was added. After stirring for 5 hours, the solution was allowed to stand overnight. The resulting precipitate was removed, and the filtrate was concentrated at reduced pressure, and purified by silicachromatography (chloroform/methanol) to afford 0.72 g of oily 2- α-[4-(4'-chlorophenoxy)phenoxy]propionylaminoethyl 2-(N-phthalimido)ethyl phosphate in a yield of 60%.

0.72 g (1.2 millimols) of the resulting product in 15 ml. of ethanol and 0.8 ml. of 100% hydrazine hydrate, was refluxed for 1.5 hours with stirring. The mixture was treated in the same way as in Example 9 to afford 0.22 g of 2- α-[4-(4'-chlorophenoxy)phenoxy]propionylamino ethylphosphoryl ethanolamine in a yield of 40%.

EXAMPLE 14

To a stirred solution of 1.54 g (10 millimols) of distilled phosphorus oxychloride in 10 ml. of dry chloroform, a mixture of 3.22 g (10 millimols) of 2-[4-(4'-chlorophenoxy)phenoxyacetylamino]ethanol and 1.4 g (11 millimols) of anhydrous quinoline in 40 ml. of dry chloroform was gradually added dropwise cooling it with ice. 30 minutes after the addition, the temperature was returned to room temperature. To the above stirred mixture, a solution of 1.91 g (10 millimols) of 2-(N-phthalimido)ethanol and 4 ml. (40 millimols) of anhydrous pyridine in 30 ml. of chloroform was gradually added dropwise under cooling again, 30 minutes later, the temperature was returned to room temperature, and the mixture was allowed to stand overnight. Then, 0.2 ml. (10 millimols) of water was added, and the mixture was stirred for 1 hour, diluted with chloroform, and shaken three times with a 0.1M potassium chloride solution. The chloroform layer was dried, concentrated at reduced pressure, and purified by silica chromatography (chloroform/methanol in a volume ratio of 95:5) to afford 4 g of oily 2-[4-(4'-chlorophenoxy)phenoxyacetylamino]ethyl 2-(N-phthalimido)ethyl phosphate in a yield of 70%.

50 ml. of ethanol and 0.6 ml. of 100% hydrazine hydrate were added to 4 g (7 millimols) of the resulting product, and the mixture was refluxed for 1.5 hours with stirring. The solution was then treated in the same way as in Example 9 to afford 0.7 g of 2-[4-(4'-chlorophenoxy)phenoxyacetylamino]ethylphosphoryl ethanolamine in a yield of 20%.

EXAMPLE 15

To a stirred solution of 6.44 g (15 millimols) of 2-[4-(4'-chlorophenoxy)phenoxyacetylamino]ethanol in 50 ml. of dry benzene, a solution of 8.3 g (54 millimols) of distilled phosphorus oxychloride and 30 ml. of dry benzene was gradually added while cooling it with ice. 30 minutes after the addition, the temperature was returned to room temperature, and the mixture was further stirred for 4 hours. Then, it was concentrated at reduced pressure. The residue was dissolved in benzene, and the solution was concentrated to remove excessive phosphorus oxychloride. The procedure was repeated five times to afford 8.75 g of oily 2-[4-(4'-chlorophenoxy)phenoxyacetylamino]ethyl dichlorophosphate in a quantitative yield.

With stirring, a solution of 7.76 g (18 millimols) of the resulting product in 25 ml. of chloroform was added dropwise to a solution of 1.91 g (10 millimols) of 2-(N-phthalaimdo)ethanol and 4 ml. (40 millimols) of anhydrous pyridine in 15 ml. of dry chloroform while cooling it with ice. 30 minutes after the addition, the temperature was returned to room temperature, and the mixture was stirred for 5 hours and then allowed to stand overnight. The mixture was then diluted with chloroform, and shaken three times with a 0.1 M potassium chloride solution. The chloroform layer was dried, concentrated at reduced pressure, and purified by silica-chromatography (chloroform/methanol in a volume ratio of 95:5) to afford 5.8 g of 2-[4-(4'-chlorophenoxy)phenoxyacetylamino]ethyl 2-(N-phthalimido)ethyl phosphate in a quantitative yield.

Then, 80 ml. of ethanol and 0.8 ml. of 100% hydrazine hydrate were added to 5.8 g (10 millimols) of the resulting product. The mixture was refluxed for 1.5 hours with stirring, and then treated in the same way as in Example 9 to afford 0.8 g of 2-[4-(4'-chlorophenoxy)phenoxyacetylamino]ethylphosphoryl ethanolamine in a yield of 19%.

EXAMPLE 16

Tablets were prepared from the following formulation.

|  | Amount (mg) |
|---|---|
| 2-(Octadeca-9,12,15-trienoylamino)-ethylphosphoryl ethanolamine | 20.0 |
| Lactose | 86.0 |
| Corn starch | 86.0 |
| Corn starch (for paste) | 7.0 |
| Magnesium stearate | 1.0 |
| Total | 200.0 |

2-(Octadeca-9,12-15-trienoylamino)ethylphosphoryl ethanolamine obtained in Example 1, lactose and corn starch were mixed, and granulated with starch paste. The mixture was passed through a No. 12 mesh screen. The wet granulate was dried overnight in an oven at 40° C. The dried granulate was passed through a No. 16 mesh screen, and mixed with the magnesium stearate. The mixture was compressed into flat-faced tablets each containing about 12.5 mg of the active substance.

EXAMPLE 17

Tablets were prepared from the following formulation.

|  | Amount (mg) |
|---|---|
| 2-[4-(4'-chlorophenoxy)phenoxyacetylamino]ethylphosphoryl ethanolamine | 15.0 |
| Microcrystalline cellulose | 75.0 |
| Corn starch | 8.0 |
| Light silicic anhydride | 1.0 |
| Magnesium stearate | 1.0 |
| Total | 100.0 |

EXAMPLE 18

The following experiments were conducted in order to examine the renin-inhibitory activities, antihypertensive activities, and cholesterol-lowering activities of the compounds of this invention.

The following eight compounds in accordance with the present invention and two comparison compounds disclosed in Folia Pharmacologica Japonica, Vol. 69, No. 6, p. 339 p, 1973 were used as test compounds.

[Compounds of this invention]

1. 2-(Octadeca-9,12,15-trienoylamino)ethylphosphoryl ethanolamine
2. 3-(Octadeca-9,12,15-trienoylamino)propylphosphoryl ethanolamine
3. 2-(Octadeca-9,12-dienoylamino)ethylphosphoryl ethanolamine
4. 3-(Octadeca-9,12-dienoylamino)propylphosphoryl ethanolamine
5. 2-[4-(4'-chlorophenoxy)phenoxyacetylamino]ethylphosphoryl ethanolamine
6. 2-$\alpha$-[4-(4'-chlorophenoxy)phenoxy]propionylamino ethylphosphoryl ethanolamine
7. 3-[4-(4'-chlorophenoxy)phenoxyacetylamino]propylphosphoryl ethanolamine
8. 3-$\alpha$-[4-(4'-chlorophenoxy)phenoxy]propionylamino propylphosphoryl ethanolamine

[Compounds disclosed in Folia Pharmacologica Japonica, above cited]

a. rac-2-Octadecanoyl-3-(eicosa-5,8,11,14-tetraenoyl)glycero-1-phosphoryl ethanolamine
b. rac-2-Octadecanoyl-3-(octadeca-9,12,15-trienoyl)glycero-1-phosphoryl ethanolamine 1. Renin-inhibitory activity:

S. Sen and R. R. Smeby et al. previously reported on the renin-inhibitory activity of phospholipid isolated from the plasma and kidney of a dog in vitro (Biochemistry, Vol. 6, No. 6, p. 1572, 1967, and Circulation Research, Vol. 21, p. II–129, 1967).

[METHOD I]

Renin (see E. Haas et al. Circulation Research, Vol. 19, p. 739, 1966 and Vol. 31, p. 65, 1972) was incubated in Angiotensinogen at 37° C. for 2 to 6 hours. Similarly, renin was incubated under the same conditions in the presence of 0.313 to 2.5 mg/ml. of each of the test compounds listed above. The amount of Angiotensin I was measured by radioimmunoassay (RIA) (E. Haber et al., J. Clin. Endocrinol., Vol. 29, p. 1349, 1969), and made the renin activity. On the other hand, the rate of inhibiting the formation of Angiotensin I in percent in the presence of each of the test compounds was determined, and made the renin-inhibitory activity.

[METHOD II]

High renin plasma prepared by constriction of the renal artery of a dog anesthetized with Nembutal (the plasma which when incubated at 37°40 C. for 6 hours, yields 30 to 120 mg/ml. of Angiotensin I) was incubated at 37° C. for 2 to 6 hours in the same way as in Method I, and also under the same conditions in the presence of 1.25 mg/ml. of each of the test compounds. In the same manner as in Method I, the rate of inhibiting the formation of Angiotensin I was determined, and made the renin-inhibitory activity.

The results are shown in Table 1 (the rate of inhibiting the formation of Angiotensin I, as determined by Method I, when the plasma was incubated at 37° C. for 2, 4 and 6 hours respectively), and Table 2 (the rate of inhibiting the formation of Angiotensin I when the plasma was incubated at 37° C. for 4 hours, with the compound concentration of 1.25 mg/ml.)

Table 1

| Test compound | Concentration of the compound (mg/ml.) | Rate of inhibiting the formation of Angiotension I, (%) Incubating time (hours) | | |
|---|---|---|---|---|
|  |  | 2 | 4 | 6 |
| Compound (2) | 2.5 | 93 (%) | 100 (%) | 100 (%) |
|  | 1.25 | 75 | 78 | 80 |
|  | 0.625 | 50 | 45 | 47 |
|  | 0.313 | 25 | 27 | 22 |
| Compound (5) | 2.5 | 100 | 93 | 92 |
|  | 1.25 | 75 | 80 | 80 |
|  | 0.625 | 50 | 50 | 53 |
|  | 0.313 | 0 | 33 | 40 |
| Compound (6) | 2.5 | 100 | 93 | 89 |
|  | 1.25 | 75 | 78 | 67 |
|  | 0.625 | 50 | 56 | 53 |
|  | 0.313 | 25 | 33 | 33 |

Table 2

Renin-inhibiting activity when the plasma was incubated at 37°C. for 4 hours (compound concentration 1.25 mg/ml.)

| Test compound | Rate of inhibiting the formation of Angiotensin I determined by Method I (%) | Rate of inhibiting the formation of Angiotensin I determind by Methid II(%) |
|---|---|---|
| (1) | 61 | 50 |
| (2) | 78 | 59 |
| (3) | 25 | 21 |
| (4) | 29 | 24 |
| (5) | 78 | 56 |
| (6) | 78 | 55 |
| (7) | 64 | 52 |
| (8) | 67 | 51 |
| (a) | < 10 | 25 |
| (b) | < 10 | 25 |

2. Antihypertensive activity:

An aqueous solution or suspension in peanut oil of each test compound as administered intramuscularly (i.m.) or orally (p.o.) at a dose of 30 to 100 mg/kg (body weight)/day once every morning over the period of 6 to 7 days.

The blood pressure of each rat was measured daily before and 5 hours after each administration. Furthermore, the blood pressure was measured every morning after drug withdrawal over a period of 3 to 6 days. Changes of the blood pressure from the value before drug administration on the first day shown in Table 3 and Table 4. The minus and/or plus sign show that the blood pressure decreased and/or increased, respectively, from the initial value before drug administration on the first day throughout the examination.

Test compounds (1)–(4) decreased the blood pressure of renal hypertensive rats with a dose of 30 mg/kg/day i.m.. The effects of compounds (1)–(4) were more potent when the decrease rate of blood pressure at 24 hours after each administration was compared with those of compounds (a) and (b) (Table 3). The antihypertensive rats with a dose of 100 mg/kg/day p.o.. But, the compound (a) did not show such an effect in the case of oral administration (Table 4).

Table 3

| Test compound | Time observed (hours) | Changes of blood pressure (mmHg) days | | | | | | Changes of blood pressure after drug withdrawal (mmHg) days | | |
|---|---|---|---|---|---|---|---|---|---|---|
| | | 1st | 2nd | 3rd | 4th | 5th | 6th | 1st | 2nd | 3rd |
| (1) | 0* | 0 | −6 | −8 | −16 | −20 | −24 | −21 | −13 | −4 |
| | 5** | −17 | −33 | −35 | −37 | −35 | −35 | | | |
| (2) | 0 | 0 | −1 | −20 | −22 | −23 | −29 | −34 | −21 | −7 |
| | 5 | −17 | −26 | −31 | −34 | −39 | −44 | | | |
| (3) | 0 | 0 | −1 | −8 | −23 | −27 | −35 | −39 | −8 | −1 |
| | 5 | −12 | −9 | −17 | −38 | −39 | −48 | | | |
| (4) | 0 | 0 | −7 | −12 | −22 | −28 | −27 | −29 | −12 | −2 |
| | 5 | −15 | −20 | −27 | −37 | −41 | −41 | | | |
| (a) | 0 | 0 | ±0 | −5 | −5 | −13 | −13 | −14 | −3 | −1 |
| | 5 | −26 | −35 | −29 | −34 | −33 | −43 | | | |
| (b) | 0 | 0 | −4 | −8 | −7 | −8 | −10 | −11 | −2 | −1 |
| | 5 | −32 | −25 | −34 | −39 | −44 | −47 | | | |

*:immediately before each administration
**:5 hours after each administration

Table 4

| Test compound | Time observed (hours) | Changes of blood pressure (mmHg) days | | | | | | | Charges of blood pressure after drug withdrawal (mmHg) days | | | | | |
|---|---|---|---|---|---|---|---|---|---|---|---|---|---|---|
| | | 1st | 2nd | 3rd | 4th | 5th | 6th | 7th | 1st | 2nd | 3rd | 4th | 5th | 6th |
| (5) | 0* | 0 | ±0 | −17 | −21 | −34 | −37 | −40 | −49 | −34 | −26 | −21 | −15 | −7 |
| | 5** | +1 | −9 | −44 | −41 | −43 | −49 | −49 | | | | | | |
| (6) | 0 | 0 | +4 | −14 | −18 | −27 | −34 | −36 | −37 | −32 | −18 | −8 | −2 | +1 |
| | 5 | −9 | −4 | −25 | −27 | −41 | −47 | −51 | | | | | | |
| (7) | 0 | 0 | −3 | −3 | −10 | −10 | −11 | −18 | −19 | −11 | −5 | −5 | −3 | −1 |
| | 5 | −6 | −10 | −18 | −19 | −21 | −25 | −28 | | | | | | |
| (8) | 0 | 0 | +5 | −6 | −10 | −10 | −9 | −13 | −22 | −12 | −5 | +2 | +1 | +1 |
| | 5 | +4 | −1 | −13 | −16 | −16 | −23 | −25 | | | | | | |
| (a) | 0 | 0 | +1 | +2 | +1 | +2 | +1 | +1 | | | | | | |
| | | +2 | +5 | −2 | ±0 | +2 | ±0 | +2 | | | | | | |

*immediately before each administration
**5 hours after each administration

3. Cholesterol-lowering activity:

The effect of each of the test compounds on the plasma cholesterol level was examined in rats according to a slightly modified form of the C. M. Greenberg et al. method described in Am. J. Physiol., Vol. 202 (1961), p. 732. Rats were treated once a day with a 100 mg/Kg oral dose for 5 consecutive days instead of 7 days.

Some of the compounds of the invention were found to have decreasing potencies on the plasma cholesterol level similarly to the known substances.

The results are shown in Table 5.

Table 5

| Test compound | Cholesterol-lowering activity (%) |
|---|---|
| (5) | 48.6 |
| (6) | 48.1 |
| (a) | 0 |
| (b) | 0 |

What we claim is:

1. ω-(N-Acylamino)alkylphosphoryl ethanolamines of the general formula

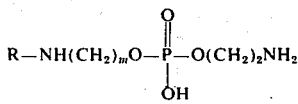

wherein R is octadeca-9,12-dienoyl, octadeca-9,12,15-trienoyl, 4-(4'-chlorophenoxy)phenoxyacetyl or α-[4-(4'-chlorophenoxy)phenoxy]propionyl, and m is 2 or 3, or their pharmaceutically acceptable acid addition salts.

2. The ω-(N-acylamino)alkylphosphoryl ethanolamines or their pharmaceutically acceptable acid addition salts of claim 1 wherein R is octadeca-9,12-dienoyl or octadeca-9,12,15-trienoyl.

3. The ω-(N-acylamino)alkylphosphoryl ethanolamines or their pharmaceutically acceptable acid addition salts of claim 1 wherein R is 4-(4'-chlorophenoxy)-phenoxyacetyl or α-[4-(4'-chlorophenoxyphenoxy]-propionyl.

4. 3-(Octadeca-9,12,15-trienoylamino)propylphosphoryl ethanolamine or its pharmaceutically acceptable acid addition salts.

5. 3-(Octadeca-9,12-dienoylamino)propylphosphoryl ethanolamine or its pharmaceutically acceptable acid addition salts.

6. 2-[4-(4'-chlorophenoxy)phenoxyacetylamino]ethylphosphoryl ethanolamine or its pharmaceutically acceptable acid addition salts.

7. 2- α-[4-(4'-chlorophenoxy)phenoxy]propionylamino ethylphosphoryl ethanolamine or its pharmaceutically acceptable acid addition salts.

8. A pharmaceutical composition for the prevention and treatment of hypertension comprising a mixture of the ω-(N-acylamino) alkylphosphoryl ethanolamine or its pharmaceutically acceptable acid addition salt, as defined in claim 1, as an active ingredient, and a pharmaceutically acceptable carrier wherein the amount of said active ingredient is about 10 to 1500 mg in terms of a dosage unit per day.

9. The pharmaceutical composition of claim 8 in a form adaptable for oral administration wherein the amount of said active ingredient is 100 to 1500mg in terms of a dosage unit per day.

10. The pharmaceutical composition of claim 8 in a form adaptable for parenteral administration wherein the amount of said active ingredient is about 10 to 150 mg in terms of a dosage unit per day.

11. The pharmaceutical composition of claim 8 wherein said active compound is 3-(octadeca-9,12,15-trienoylamino)propylphosphoryl ethanolamine or a pharmaceutically acceptable acid addition salt thereof.

12. The pharmaceutical composition of claim 8 wherein said active compound is 3-(octadeca-9, 12-dienoylamino) propylphosphoryl ethanolamine or a pharmaceutically acceptable acid addition salt thereof.

13. The pharmaceutical composition of claim 8 wherein said active compound is 2-[4-(4'-chlorophenoxy)phenoxyacetylamino] ethyl phosphoryl ethanolamine or a pharmaceutically acceptable acid addition salt thereof.

14. The pharmaceutical composition of claim 8 wherein said active compound is 2- α-[4-(4'-chlorophenoxy) phenoxy]propionyl amino ethylphosphoryl ethanolamine or a pharmaceutically acceptable acid addition salt thereof.

15. A method for treating hypertension in humans which comprises orally administering to said human from about 2 to 30 mg per kilogram of body weight per day of the ω-(N-acylamino) alkylphosphoryl ethanolamine or its pharmaceutically acceptable acid addition salt, as defined in claim 1, either alone or in admixture with a pharmaceutically acceptable carrier.

16. The method of claim 15 wherein said ω-(N-acylamino) alkyl-phosphoryl ethanolamine is 3-(octadeca-9, 12, 15-trienoylamino) propylphosphoryl ethanolamine or a pharmaceutically acceptable acid addition salt thereof.

17. The method of claim 15 wherein said ω-(N-acylamino) alkyl-phosphoryl ethanolamine is 3-(octadeca-9, 12-dienoylamino) propylphosphoryl ethanolamine or a pharmaceutically acceptable acid addition salt thereof.

18. The method of claim 15 wherein said ω-(N-acylamino) alkyl-phosphoryl ethanolamine is 2-[4-(4'-chlorophenoxy)phenoxyacetylamino] ethyl phosphoryl ethanolamine or a pharmaceutically acceptable acid addition salt thereof.

19. The method of claim 15 wherein said ω-(N-acylamino) alkyl-phosphoryl ethanolamine is 2- α-[4-(4'-chlorophenoxy) phenoxy] propionyl amino ethylphosphoryl ethanolamine or a pharmaceutically acceptable acid addition salt thereof.

20. A method for treating hypertension in humans which comprises parenterally administering to said human from about 0.2 to 3 mg per kilogram of body weight per day of the ω-(N-acylamino)alkylphosphoryl ethanolamine or its pharmaceutically acceptable acid addition salt, as defined in claim 1, either alone or in admixture with a pharmaceutically acceptable carrier.

21. The method of claim 20 wherein said ω-(N-acylamino) alkyl-phosphoryl ethanolamine is 3-(octadeca-9, 12, 15-trienoylamino) propylphosphoryl ethanolamine or a pharmaceutically acceptable acid addition salt thereof.

22. The method of claim 20 wherein said ω-(N-acylamino) alkyl-phosphoryl ethanolamine is 3-(octadeca-9, 12-dienoylamino) propylphosphoryl ethanolamine or a pharmaceutically acceptable acid addition salt thereof.

23. The method of claim 20 wherein said ω-(N-acylamino) alkyl-phosphoryl ethanolamine is 2-[4-(4'λ chlorophenoxy)phenoxyacetylamino] ethyl phosphoryl ethanolamine or a pharmaceutically acceptable acid addition salt thereof.

24. The method of claim 20 wherein said ω-(N-acylamino) alkyl-phosphoryl ethanolamine is 2- α-[4-(4'-chlorophenoxy)phenoxyl]propionyl amino ethylphosphoryl ethanolamine or a pharmaceutically acceptable acid addition salt thereof.

* * * * *

UNITED STATES PATENT AND TRADEMARK OFFICE
CERTIFICATE OF CORRECTION

PATENT NO. : 3,985,875
DATED : October 12, 1976
INVENTOR(S) : Kouji Hayashi et al.

It is certified that error appears in the above-identified patent and that said Letters Patent are hereby corrected as shown below:

Claim 3, line 4, delete "α-[4-(4'-chlorophenoxyphenoxy]-", insert
-- α-[4-(4'-chlorophenoxy)phenoxy]- --

Claim 23, line 2, delete "2-[4-(4'λ", insert -- 2-[4-(4'- --

Signed and Sealed this

First Day of February 1977

[SEAL]

*Attest:*

RUTH C. MASON
*Attesting Officer*

C. MARSHALL DANN
*Commissioner of Patents and Trademarks*